(12) United States Patent
Crawford

(10) Patent No.: US 6,780,169 B2
(45) Date of Patent: *Aug. 24, 2004

(54) SAFETY SHIELD ASSEMBLY

(75) Inventor: Jamieson William Maclean Crawford, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/171,254

(22) Filed: Jun. 12, 2002

(65) Prior Publication Data

US 2002/0151853 A1 Oct. 17, 2002

Related U.S. Application Data

(63) Continuation-in-part of application No. 09/378,976, filed on Aug. 23, 1999, now Pat. No. 6,440,104.

(51) Int. Cl.[7] .............................................. A61M 5/00
(52) U.S. Cl. ........................................ 604/110; 128/898
(58) Field of Search .......................... 604/110, 181–182, 604/187–188, 192, 197, 199, 239–241, 243, 263–264, 272, 905; 128/919; 600/573, 576

(56) References Cited

U.S. PATENT DOCUMENTS

| | | |
|---|---|---|
| 1,779,451 A | 10/1930 | Sponsel |
| 2,004,050 A | 6/1935 | Kerk |
| 2,700,385 A | 1/1955 | Ortiz |
| 2,836,942 A | 6/1958 | Miskel |
| 2,854,976 A | 10/1958 | Heydrich |
| 2,953,243 A | 9/1960 | Roehr |
| 3,021,942 A | 2/1962 | Hamilton |
| 3,073,307 A | 1/1963 | Stevens |
| 3,074,542 A | 1/1963 | Myerson et al. |
| 3,255,873 A | 6/1966 | Speelman |
| 3,294,231 A | 12/1966 | Vanderbeck |
| 3,323,523 A | 6/1967 | Scislowicz et al. |
| 3,329,146 A | 7/1967 | Waldman, Jr. |
| 3,333,682 A | 8/1967 | Burke |
| 3,367,488 A | 2/1968 | Hamilton |
| 3,485,239 A | 12/1969 | Vanderbeck |
| 3,537,452 A | 11/1970 | Wilks |
| 3,610,240 A | 10/1971 | Hanutuneian |
| 3,658,061 A | 4/1972 | Hall |
| 3,828,775 A | 8/1974 | Armel |
| 3,890,971 A | 6/1975 | Leeson et al. |
| 3,904,033 A | 9/1975 | Haerr |
| 3,934,722 A | 1/1976 | Goldberg |

(List continued on next page.)

FOREIGN PATENT DOCUMENTS

| | | |
|---|---|---|
| GB | 1 233 302 | 5/1971 |
| GB | 2 239 604 | 7/1991 |
| GB | 2 239 607 | 7/1991 |
| GB | 2 240 273 | 7/1991 |
| GB | 2 240 477 | 8/1991 |
| WO | WO 87/07162 | 12/1987 |
| WO | WO 90/01348 | 2/1990 |
| WO | WO 91/09637 | 7/1991 |
| WO | WO 91/09638 | 7/1991 |
| WO | WO 91/09639 | 7/1991 |
| WO | WO 93/16745 | 9/1993 |

*Primary Examiner*—Loan H. Thanh
(74) *Attorney, Agent, or Firm*—Gereald E. Hespos; Anthony J. Casella

(57) ABSTRACT

The present invention is a safety shield assembly having a shield and a collar for connecting the shield to a fluid handling device whereby the shield may be pivoted with respect to the collar. Preferably, the safety shield assembly may be used with a needle assembly, an intravenous infusion set a syringe, a catheter or other fluid handling devices or assemblies that contain piercing elements.

25 Claims, 17 Drawing Sheets

U.S. PATENT DOCUMENTS

| | | |
|---|---|---|
| 3,968,876 A | 7/1976 | Brookfield |
| 4,113,090 A | 9/1978 | Carstens |
| 4,139,009 A | 2/1979 | Alvarez |
| 4,175,008 A | 11/1979 | White |
| 4,300,678 A | 11/1981 | Gyure et al. |
| RE31,086 E | 11/1982 | Johnson, Jr. et al. |
| 4,375,849 A | 3/1983 | Hanifl |
| 4,430,082 A | 2/1984 | Schwabacher |
| 4,592,744 A | 6/1986 | Jagger et al. |
| 4,634,428 A | 1/1987 | Cuu |
| 4,643,722 A | 2/1987 | Smith, Jr. |
| 4,659,330 A | 4/1987 | Nelson et al. |
| 4,664,249 A | 5/1987 | Gherardi |
| 4,664,259 A | 5/1987 | Landis |
| 4,664,654 A | 5/1987 | Strauss |
| 4,671,408 A | 6/1987 | Raines et al. |
| 4,681,567 A | 7/1987 | Masters et al. |
| 4,695,274 A | 9/1987 | Fox |
| 4,702,738 A | 10/1987 | Spencer |
| 4,723,943 A | 2/1988 | Spencer |
| 4,728,320 A | 3/1988 | Chen |
| 4,728,321 A | 3/1988 | Chen |
| 4,731,059 A | 3/1988 | Wanderer et al. |
| 4,735,311 A | 4/1988 | Lowe et al. |
| 4,735,618 A | 4/1988 | Hagen |
| 4,737,144 A | 4/1988 | Choksi |
| 4,738,663 A | 4/1988 | Bogan |
| 4,743,233 A | 5/1988 | Schneider |
| 4,746,008 A | 5/1988 | Heverly et al. |
| 4,747,836 A | 5/1988 | Luther |
| 4,747,837 A | 5/1988 | Hauck |
| 4,772,272 A | 9/1988 | McFarland |
| 4,778,453 A | 10/1988 | Lopez |
| 4,781,697 A | 11/1988 | Slaughter |
| 4,782,841 A | 11/1988 | Lopez |
| 4,790,828 A | 12/1988 | Dombrowski et al. |
| 4,793,484 A | 12/1988 | Schoettle |
| 4,795,432 A | 1/1989 | Karczmer |
| 4,795,443 A | 1/1989 | Permenter et al. |
| 4,801,295 A | 1/1989 | Spencer |
| 4,804,372 A | 2/1989 | Laico et al. |
| 4,813,426 A | 3/1989 | Haber et al. |
| 4,816,022 A | 3/1989 | Poncy |
| 4,816,024 A | 3/1989 | Sitar et al. |
| 4,819,659 A | 4/1989 | Sitar |
| 4,820,277 A | 4/1989 | Norelli |
| 4,826,490 A | 5/1989 | Byrne et al. |
| 4,826,491 A | 5/1989 | Schramm |
| 4,838,871 A | 6/1989 | Luther |
| 4,842,587 A | 6/1989 | Poncy |
| 4,846,796 A | 7/1989 | Carrell et al. |
| 4,850,968 A | 7/1989 | Romano |
| 4,850,976 A | 7/1989 | Heinrich et al. |
| 4,850,977 A | 7/1989 | Bayless |
| 4,850,978 A | 7/1989 | Dudar et al. |
| 4,850,994 A | 7/1989 | Zerbst et al. |
| 4,850,996 A | 7/1989 | Cree |
| 4,858,607 A | 8/1989 | Jordan et al. |
| 4,863,434 A | 9/1989 | Bayless |
| 4,863,435 A | 9/1989 | Sturman et al. |
| 4,863,436 A | 9/1989 | Glick |
| 4,867,746 A | 9/1989 | Dufresne |
| 4,872,552 A | 10/1989 | Unger |
| 4,874,383 A | 10/1989 | McNaughton |
| 4,874,384 A | 10/1989 | Nunez |
| 4,883,469 A | 11/1989 | Glazier |
| 4,886,503 A | 12/1989 | Miller |
| 4,888,001 A | 12/1989 | Schoenberg |
| 4,892,107 A | 1/1990 | Haber |
| 4,892,521 A | 1/1990 | Laico et al. |
| 4,900,309 A | 2/1990 | Netherton et al. |
| 4,909,791 A | 3/1990 | Norelli |
| 4,909,792 A | 3/1990 | Norelli |
| 4,921,096 A | 5/1990 | McFarlane |
| 4,927,018 A | 5/1990 | Yang et al. |
| 4,944,397 A | 7/1990 | Miller |
| 4,966,591 A | 10/1990 | Yuen |
| 4,976,699 A | 12/1990 | Gold |
| 4,982,842 A | 1/1991 | Hollister |
| 5,011,475 A | 4/1991 | Olson |
| 5,011,479 A | 4/1991 | Le et al. |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,151,089 A | 9/1992 | Kirk, III et al. |
| 5,154,285 A | 10/1992 | Hollister |
| 5,188,611 A | 2/1993 | Orgain |
| 5,197,954 A | 3/1993 | Cameron |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,277,311 A | 1/1994 | Hollister |
| 5,312,369 A | 5/1994 | Arcusin et al. |
| 5,401,251 A | 3/1995 | Hui |
| 5,405,332 A | 4/1995 | Opalek |
| 5,423,765 A | 6/1995 | Hollister |
| 5,462,534 A | 10/1995 | Debreczeni |
| 5,485,854 A | 1/1996 | Hollister |
| 5,486,163 A | 1/1996 | Haynes |
| 5,490,841 A | 2/1996 | Landis |
| 5,509,907 A | 4/1996 | Bevilacqua |
| 5,533,984 A | 7/1996 | Parmigiani |
| 5,584,816 A | 12/1996 | Gyure et al. |
| 5,599,313 A | 2/1997 | Gyure et al. |
| 5,599,318 A | 2/1997 | Sweeney et al. |
| 5,603,699 A | 2/1997 | Shine |
| 5,632,732 A | 5/1997 | Szabo et al. |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,693,022 A | 12/1997 | Haynes |
| 5,702,369 A | 12/1997 | Mercereau |
| 5,733,265 A | 3/1998 | Bachman et al. |
| 5,807,351 A | 9/1998 | Kashmer |
| 5,836,920 A | 11/1998 | Robertson |
| 5,885,249 A | 3/1999 | Irisawa |
| 5,913,846 A | 6/1999 | Szabo |
| 5,993,426 A | 11/1999 | Hollister |
| 6,077,253 A | 6/2000 | Cosme |
| 6,080,137 A | 6/2000 | Pike |
| 6,120,482 A | 9/2000 | Szabo |
| 6,139,533 A | 10/2000 | Xia et al. |
| RE37,100 E | 3/2001 | Greenly |
| RE37,252 E | 7/2001 | Hollister |
| 6,319,232 B1 | 11/2001 | Kashmer |
| 6,328,713 B1 | 12/2001 | Hollister |
| 6,334,857 B1 | 1/2002 | Hollister et al. |

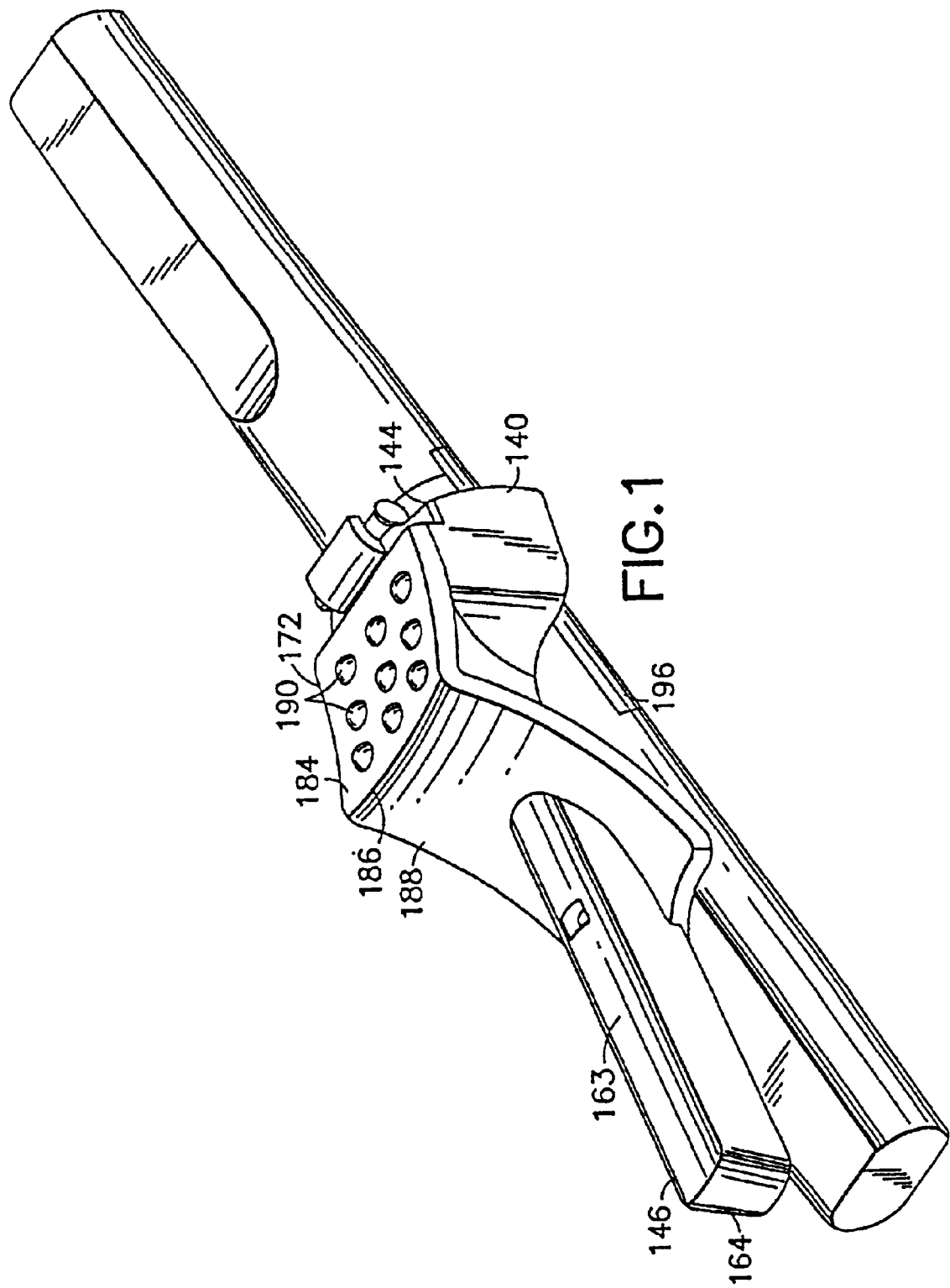

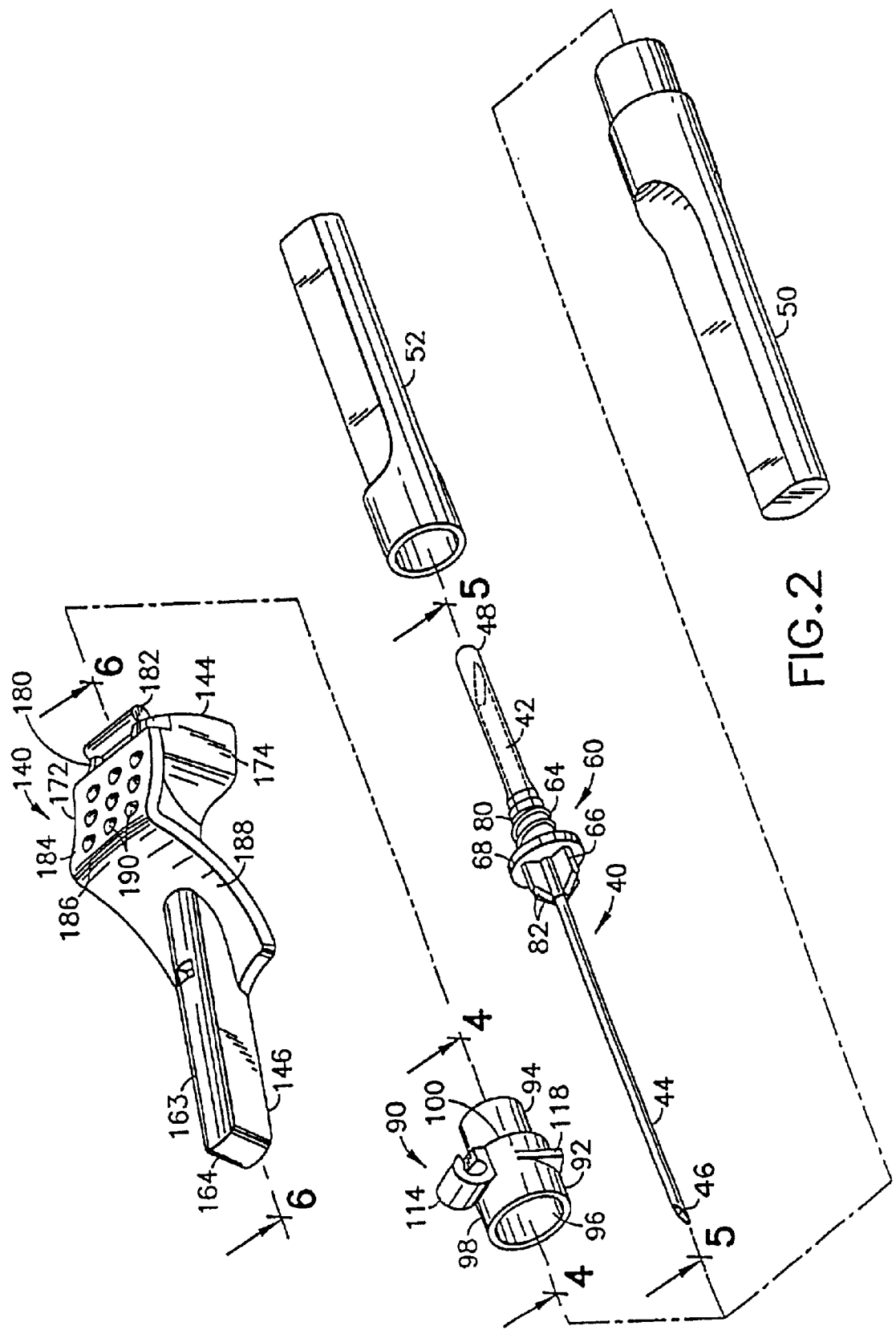

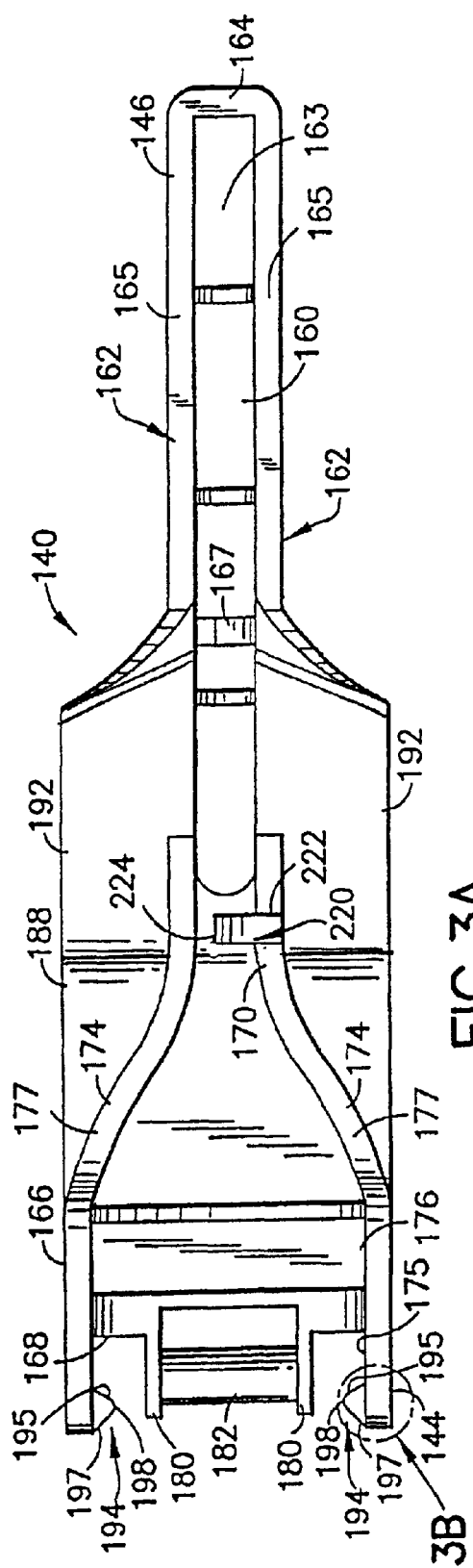
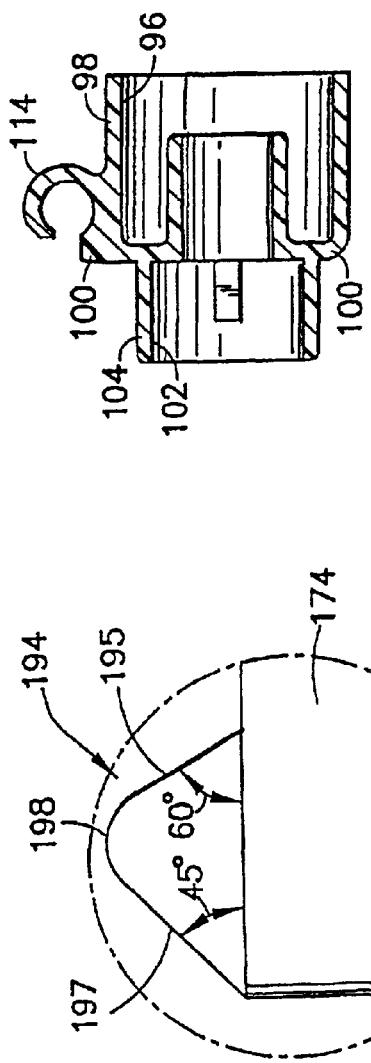
FIG.3A
FIG.3B
FIG.4

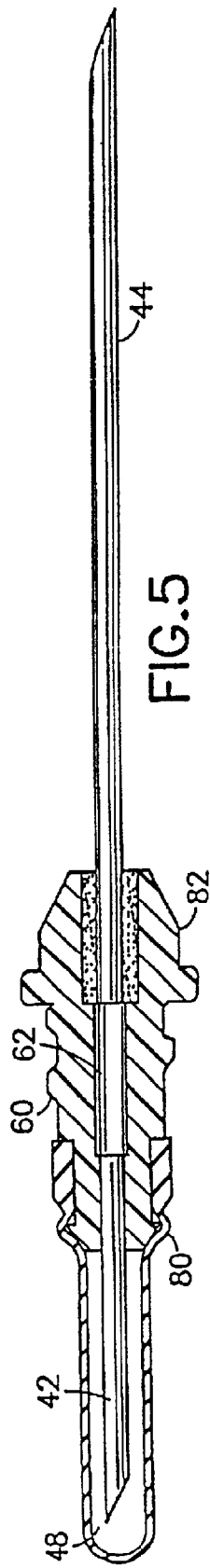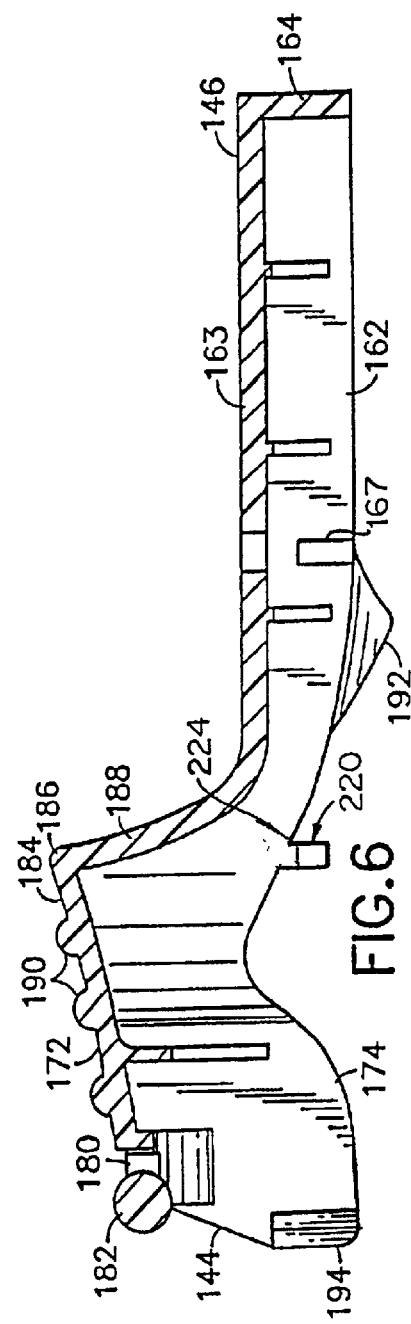

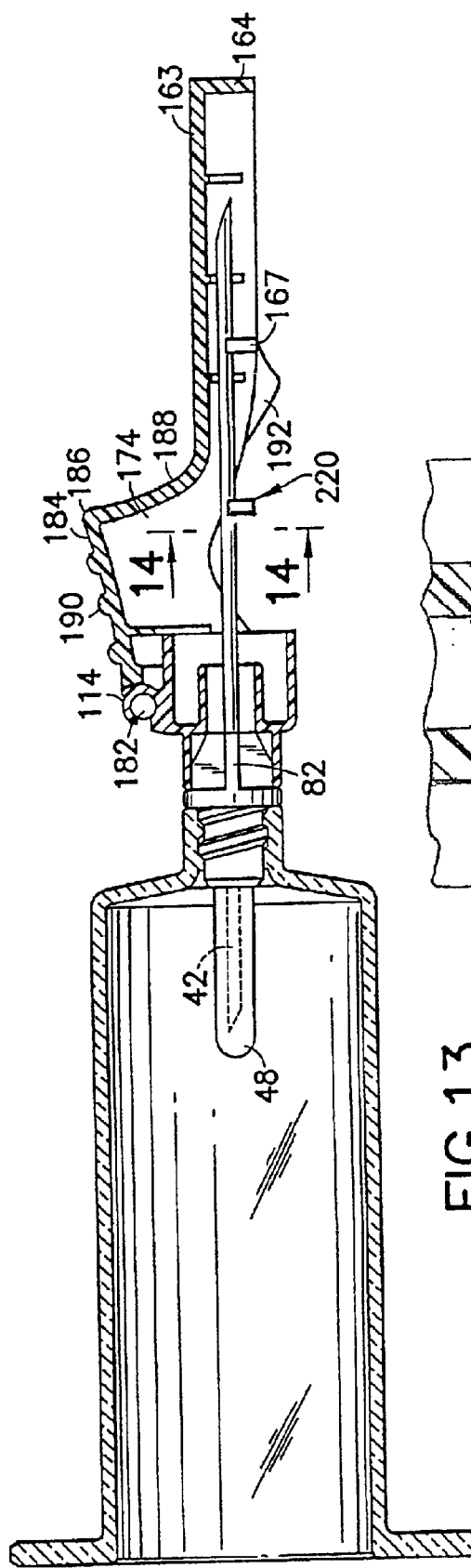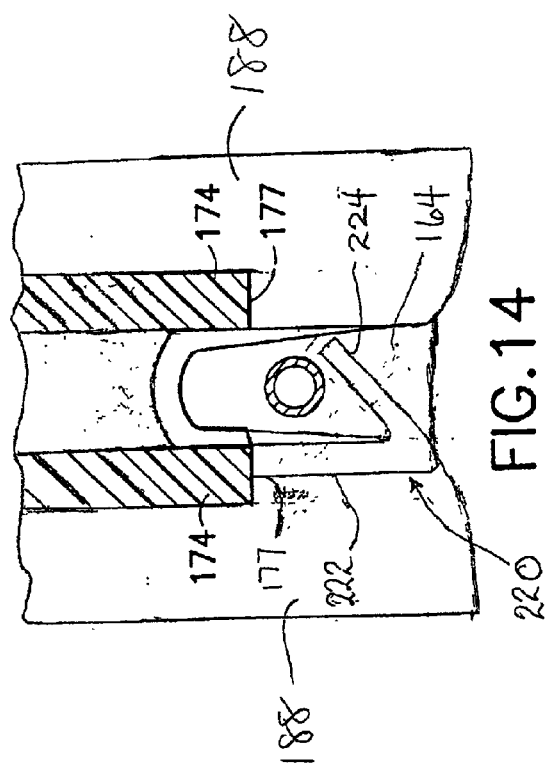
FIG. 13
FIG. 14

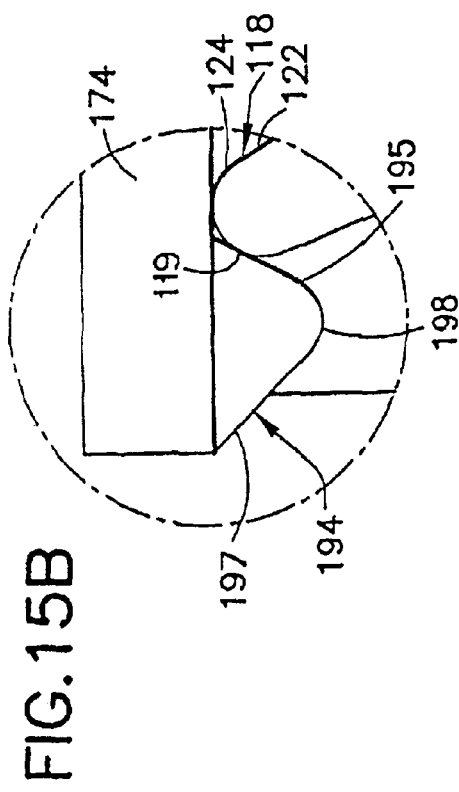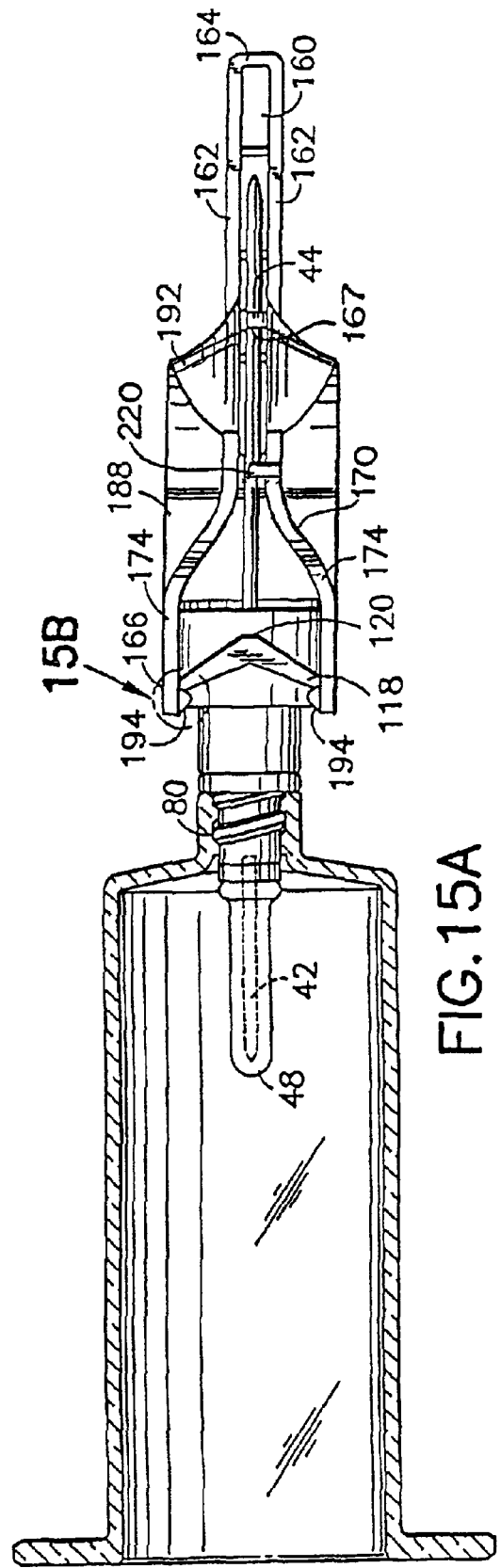

SAFETY SHIELD ASSEMBLY

RELATED APPLICATION

This application is a continuation-in-part of U.S. patent application. No. 09/378,976, filed Aug. 23, 1999 now U.S. Pat. No. 6,440,104.

1. FIELD OF THE INVENTION

The present invention relates to a shield for a needle and more particularly to a safety shield assembly that may be used in conjunction with a syringe assembly, a hypodermic needle, a needle assembly, a needle assembly with a needle holder, a blood collection needle, a blood collection set, an intravenous infusion set or other fluid handing devices or assemblies that contain piercing elements.

2. BACKGROUND OF THE INVENTION

Disposable medical devices having piercing elements for administering a medication or withdrawing a fluid, such as hypodermic needles, blood collecting needles, fluid handling needles and assemblies thereof, require safe and convenient handling. The piercing elements include, for example, pointed needle cannula or blunt ended cannula.

Safe and convenient handling of disposable medical devices is recognized by those in the medical arts so as to minimize exposure to blood borne pathogens. Safe and convenient handling of disposable medical devices results in the disposal of the medical devices intact.

As a result of this recognition, numerous devices have been developed for shielding needles after use. Many of these devices are somewhat complex and costly. In addition, many of these devices are cumbersome to use in performing procedures. Furthermore, some of the devices are so specific that they preclude use of the device in certain procedures or with certain devices and/or assemblies. For example, some devices employ very short thin needle cannulas. A shield designed to lock near the distal end of one needle cannula might not engage a much shorter needle cannula. Additionally, a shield designed to lock with a wider gauge needle cannula might be more likely to generate a spray upon engaging a much narrower needle cannula. Furthermore, it may be desirable to reduce the force required to effect shielding without reducing the audible and tactile indications of complete shielding.

Therefore, there exists a need for a safety shield assembly: (i) that is manufactured easily; (ii) that is applicable to many devices; (iii) that is simple to use with one hand; (iv) that can be disposed of safely; (v) that does not interfere with normal practices of needle use; (vi) that has tactile features whereby the user may be deterred from contacting the needle, the user may easily orient the needle with the patient and easily actuate and engage the shield assembly; (vii) that has visual features whereby the user may be deterred from contacting the needle, the user may easily orient the needle with the patient and easily actuate and engage the shield assembly; (viii) that is not bulky; (ix) that includes means for minimizing exposure to the user of residual fluid leaking from the needle; and (x) provides minimal exposure to the user because the needle shield is immediately initiated by the user after the needle is withdrawn from the patient's vein.

3. SUMMARY OF THE INVENTION

The present invention is a safety shield assembly that comprises: a shield; means for connecting the shield to a fluid handling device that contains a piercing element, such as needle; and means for pivoting the shield away from the needle; means for securely covering and/or containing the needle within the shield.

Preferably, the shield comprises a rearward end, a forward end, a slot or longitudinal opening for housing the used needle in the forward end, means for securing the needle in the slot, means for guiding the needle into the slot, means for connecting the shield and the fluid handling device, means for guiding the user's fingers to move the shield into various positions, and means for retaining the shield securely over the used needle.

Desirably, the means for connecting the shield to the fluid handling device is with a collar. Preferably, the shield is connected movably to a collar which is connected to a fluid handling device.

Preferably, the shield is connected to the collar by a hanger bar that engages with a hook arm on the collar so that the shield may be pivoted with respect to the collar into several positions. It is within the purview of the present invention to include any structure for connecting the shield to the collar so that the shield may be pivoted with respect to the collar. These structures include known mechanical hinges and various linkages, living hinges, or combinations of hinges and linkages.

Most preferably, the shield is connected to the collar by an interference fit between the hanger bar and the hook bar. Therefore, the shield always is oriented in a stable position and will not move forward or backwards unless movement of the shield relative to the hanger bar and the hook bar is initiated by the user.

Alternatively, the shield and collar may be a unitary one-piece structure. The one-piece structure may be accomplished by many methods, including molding the shield and the collar as a one-piece unit, thereby eliminating the separate shield and collar during the manufacturing or assembly process.

The assembly of the present invention may further comprise tactile and visual means for deterring the user from contacting the needle, providing easy orientation of the needle with the patient and providing the user with a guide for actuation and engagement with the shield.

The assembly of the present invention may further comprise means for minimizing exposure by the user to residual fluid leaking from a used needle. For example, a polymer material, such as a gel, may be located in the shield.

Most desirably, the assembly of the present invention is such that the cooperating parts of the assembly provide the means for the shield to move into a forward position over the needle. Thus, by simple movement of the shield into a forward position over the used needle, the assembly is ready for subsequent disposal. Therefore, the safety shield assembly of the present invention provides minimal exposure of the user to a needle because the shielding is initiated by the user immediately after the needle is withdrawn from the patient's vein.

Desirably, the assembly of the present invention may be used with a syringe assembly, a hypodermic needle, a needle assembly, a needle assembly with a needle holder, a blood collection set, an intravenous infusion set or other fluid handling devices. Preferably, the assembly of the present invention is used with a needle assembly comprising a needle and a hub. Preferably the needle is a conventional double ended needle.

Most preferably, the present invention is used with a needle assembly comprising a hub and a needle connected to the hub whereby the needle comprises a non-patient end and an intravenous end. The collar of the present invention may comprise a hook arm and the shield may be connected movably to the hook arm. Thus the shield may be pivoted with respect to the collar and moved easily into several positions.

Preferably, the collar is fitted non-rotatably with the hub of the needle assembly. Additionally, the collar includes cooperating means that mate with reciprocal means on the shield to help retain the shield in a second position, to propel the shield toward the second position and to provide a clear audible and tactile indication of complete shielding.

The shield preferably includes at least first and second cannula locks for locked engagement with the cannula when the shield is in the second position around the needle cannula. At least one cannula lock is disposed to engage a portion of a needle cannula near the respective needle hub. Thus, the at least one cannula lock is disposed to lockingly engage a short needle cannula. The at least one cannula lock preferably is substantially J-shaped, with a first leg that extends from an edge region of the shield and a second leg that projects angularly back toward the shield. The second leg of the cannula lock is disposed and configured to resiliently deflect as the shield is rotated into its second position around the needle cannula. The second leg of the cannula lock then will resiliently return toward an undeflected condition for trapping and locking the needle cannula when the shield reaches its second position. Trapping and locking of the needle cannula by the J-shaped cannula lock preferably occurs substantially simultaneously with the audible and tactile engagement of the cooperating means on the collar and the shield that provide the audible and tactile indication of shielding. The second cannula lock may have a different configuration than the first cannula lock. The second cannula lock may be disposed closer to the front or distal end of the shield and may be disposed internally on the shield.

Preferably, the collar is fitted with the hub of the needle assembly whereby the collar cannot rotate around the hub.

Alternatively, the collar and hub may be a unitary one-piece structure. The one piece structure may be accomplished by many methods including molding the collar and the hub as a one-piece unit thereby eliminating the need to separately assemble the collar to the hub during the manufacturing process.

Most preferably, the collar is fitted with the hub of the needle assembly so that the bevel surface or bevel up surface of the intravenous or distal end of the needle faces the same side of the collar when the shield is in the first position. Alignment of the collar, hub, shield and needle with the bevel surface up makes it easier to insert the needle into the patient without manipulating the assembly. The orientation of the intravenous end of the needle with the bevel up assures the user that the needle is properly oriented for use and does not require any manipulation before use. Most notably, the orientation of the shield provides a visual indication to the user of the orientation of the bevel surface of the needle.

Preferably, the shield is capable of pivoting from a first position where the intravenous end of the needle is exposed and bevel up, to an intermediate position where the needle is partially covered, to a second position where the needle is contained by the shield.

Alternatively, it is within the purview of the present invention that the shield, collar and hub is a unitary one-piece structure. The one-piece structure may be accomplished by many methods including molding the shield, collar and hub as a one-piece unit thereby eliminating the need to separately assemble the shield, collar and hub during the manufacturing process.

It is an advantage of the present invention that the shield covering the used intravenous end of the needle provides easy containment of the used needle. A further advantage of the shield is that it will only move upon initiation by the user.

The assembly of the present invention when used with a fluid handling device is also easily disposable when removed from a conventional needle holder, or other such device.

A notable attribute of the present invention is that it is easily adaptable with many devices. For example, the invention is usable with syringe assemblies, hypodermic needles, needle holders, blood collection needles, blood collection sets, intravenous infusion sets such as catheters or other fluid handling devices or assemblies that contain piercing elements.

Another notable attribute of the present invention is that the tactile and visual features deter the user from touching the needle, allow the user to easily orient the needle with the patient and guide the user to actuate and engage the shield of the assembly.

4. BRIEF DESCRIPTION OF THE DRAWINGS

FIG. 1 is a perspective view of the safety shield assembly of the present invention as connected to a needle assembly and related packaging features.

FIG. 2 is a perspective view of the unassembled pieces of FIG. 1.

FIG. 3 is a bottom view of the shield as shown in FIG. 2.

FIG. 4 is a cross sectional view of the collar as shown in of FIG. 2 taken along lines 4—4 thereof.

FIG. 5 is a cross sectional view of the needle hub as shown in FIG. 2 taken along lines 5—5 thereof.

FIG. 6 is a cross sectional view of the shield of FIG. 2 taken along lines 6—6 thereof.

FIG. 13 is a cross sectional view of the assemblies in use with a conventional needle holder as shown in FIG. 11 taken along lines 13—13 thereof.

FIG. 14 is a cross-sectional view of the assemblies of FIG. 11 taken along lines 14—14 thereof.

FIGS. 15A and 15B are bottom views of the assemblies as shown in FIG. 11.

5. DETAILED DESCRIPTION OF THE INVENTION

Figure 7:
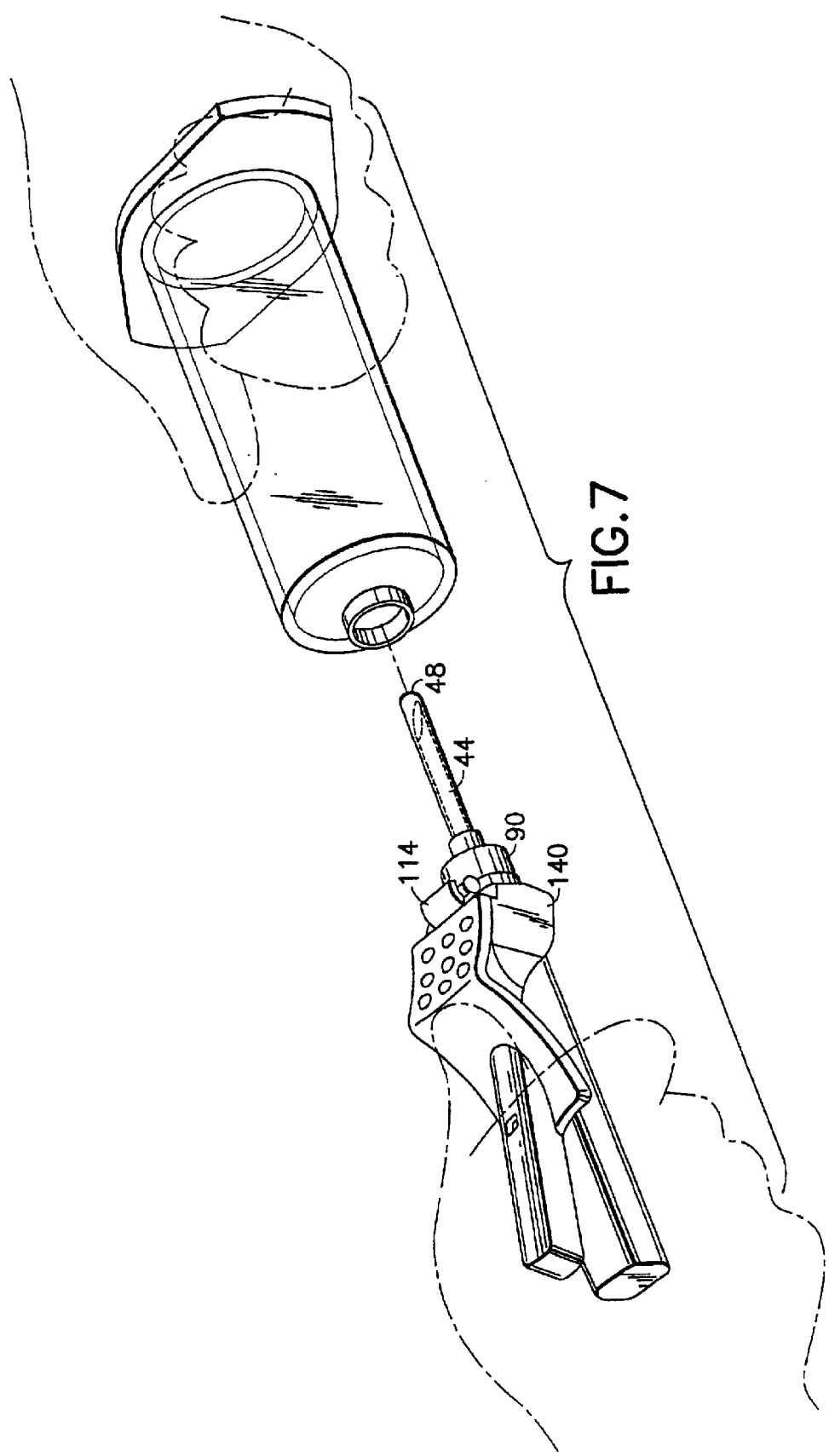
FIGS. 7–11 illustrate the use of the safety shield assembly with the needle assembly of FIG. 1 with a conventional needle holder.
Figure 8:
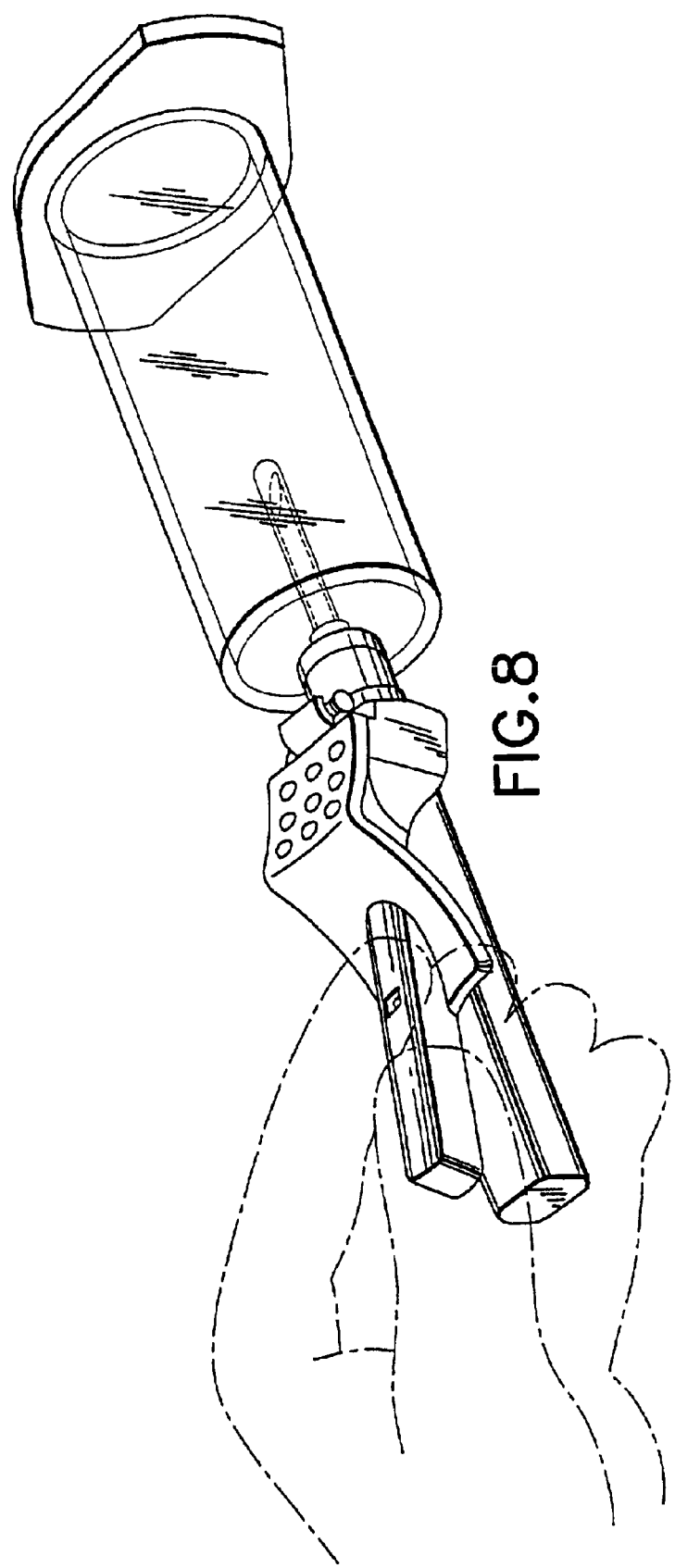

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Referring to the drawings in which like reference characters refer to like parts throughout the several views thereof, FIGS. 1 and 2 illustrate a needle assembly with the safety shield assembly of the present invention and the related packaging features. The needle assembly includes a needle 40, a hub 60, packaging features to cover the needle and a label. The safety shield assembly includes a collar 90 and a shield 140.

As shown in FIG. 2 and 5, needle 40 includes a non-patient end 42, an intravenous end 44 and a passageway 46 extending between the non-patient end and the intravenous end. An elastomeric sleeve 48 covers the non-patient end. A first rigid sleeve 50 covers the intravenous end and a second rigid sleeve 52 covers the non-patient end and the elastomeric sleeve. As shown in FIG. 1, a label 196 may also be applied to the finally assembled parts.

As shown in FIGS. 2 and 5, hub 60 includes a threaded end 64, a ribbed end 66 and passageway 62 extending between the threaded end and the ribbed end. Threaded end 64 and ribbed end 66 are separated by flange 68. Non-patient end 42 of needle 40 extends from threaded end 64 and intravenous end 44 of needle 40 extends from ribbed end 66. Preferably, threaded end 64 comprises male threads 80 for mounting the hub on a conventional needle holder and ribbed end 66 comprises male ribs 82 for connecting the hub and collar 90.

As shown in FIGS. 2 and 4, collar 90 includes a forward skirt 92 and a rearward skirt 94. Forward skirt 92 is cylindrical and comprises an inner circumferential surface 96 and an outer circumferential surface 98. Forward shirt 92 mates with rearward skirt 94 at a shoulder 100. Rearward skirt 94 is cylindrical and comprises an inner circumferential surface 102 and an outer circumferential surface 104 and extends from shoulder 100 opposite of forward skirt 92. The inner diameter of forward skirt 92 is larger than the inner diameter of rearward skirt 94. Alternatively, the inner diameters for collar 90 can be equal. A hook 114 extends from outer circumferential surface 98 of forward skirt 92. Additionally a chevron-shaped protrusion 118 projects outwardly from outer circumferential surface 98 of forward skirt 92 at a side opposite hook 114. The chevron-shape protrusion 118 is substantially symmetrically formed and has an peak 120 pointed toward forward skirt 92 and ramp surfaces 122 that diverge symmetrically from peak 120 toward rearward skirt 94. Ramp surfaces 122 terminate at rounded ends 124 at the outer side and proximal extremes of chevron-shaped protrusion 118. Rounded ends 124 extend continuously into the proximal side of chevron-shaped protrusion 118 facing toward rearward skirt 94.

As shown in FIGS. 2 and 6, shield 140 comprises a rearward end 144 and a forward end 146.

Forward end 146 of shield 140 includes a slot or longitudinal opening 160 formed by sidewalls 162 that extend downwardly from top wall 163 and run substantially opposite of one another in parallel along the length of slot 160 towards forward end wall 164. Slot 160 is slightly wider than needle 40. Sidewalls 162 include bottom edges 165 that extend substantially parallel to one another and parallel to top wall 163.

A first cannula lock 167 is located at one of sidewalls 162 and is configured to secure the used needle. First cannula lock 167 extends from a location on a first of the sidewalls 162 adjacent the bottom edge 165 thereof and projects angularly toward the opposed sidewall 162 and toward the top wall 163. The projection of the cannula lock 167 from the respective sidewall 162 preferably exceeds half the distance between the respective sidewalls. First cannula lock 167 is deflectable by the needle when the needle enters slot 160. Once the needle passes the end of first cannula lock 167, the first cannula lock moves back to its original position, whereby the needle is permanently trapped in slot 160 by first cannula lock 167.

Rearward end 144 of shield 140 defines a collar engaging area 166 that is a continuation of slot 160. Collar engaging area 166 includes a rearward end 168, a forward end 170, a top finger guide area 172, sidewalls 174 that extend downwardly from top finger guide area 172, an underside area 176 dimensioned for surrounding collar 90, and extending arms 180 to support hold hanger bar 182. Sidewalls 174 are spaced apart by a major width adjacent rearward end 168. The major width is selected to enable sidewalls 174 to slide across diametrically opposite side surfaces of forward skirt 92 of collar 90. Sidewalls 174 converge, however, toward forward end 170 to define a minor distance therebetween substantially equal to the distance between sidewalls 162 at forward end 146 of shield 140. Sidewalls 174 include bottom edges 177 that face away from top finger guide area 172. As shown most clearly in FIG. 6, bottom edges 177 curve toward top finger guide area 172 at locations between rearward end 168 and forward end 170 of collar engaging area 166.

A second means for trapping a needle in slot 160 includes the generally J-shaped or V-shaped second cannula lock 220. Second cannula lock 220 include a base leg 222 projecting from the bottom edge 177 of one sidewall 174 on forward end 170 of collar engaging area 166. Base leg 222 of second cannula lock 220 is substantially coplanar with one sidewall 162 at forward end 146 of shield 140. Second cannula lock 220 further includes a needle engaging leg 224 that extends from the end of base leg 222 angularly back toward top finger guide area 172 and toward the opposed sidewall 174. Base leg 222 of second cannula lock 220 is dimensioned such that needle engaging leg 224 will engage the needle as shield 140 is pivoted to its second position around the used needle. Additionally needle engaging leg 224 is deflectable by the needle when the needle enters slot 160. Once the needle passes the end of needle engaging leg 224, the needle engaging leg 224 moves resiliently back to its original position to trap the used needle in slot 160. Thus, second cannula lock 220 cooperates with first cannula lock 167 to permanently trap the used needle in slot 160. A potential exists for an unauthorized attempt to reuse a used needle. First cannula finger lock 167 is very effective for preventing inadvertent re-exposure of the used needle and offers some resistance to an intentional effort to re-expose the used needle. However, needle 40 becomes more flexible near the tip of intravenous end 44. Hence, needle 40 will flex in response to forces generated by first cannula lock 167 during an effort to rotate shield 140 back toward the first position. Such flexure of needle 40 will cause a sliding movement of first cannula lock 167 along intravenous end 44 of needle 40, and sufficient sliding movement may enable intravenous end 44 of needle 40 to clear first cannula lock 167. Needle 40 will be bent after such an unauthorized attempt to rotate shield 140 back to the first position. However, the bent needle can be straightened and may be functional by the unauthorized user. The second cannula lock 220, however, is much closer to hub 60, and hence on a much less flexible part of needle 40. Furthermore, second cannula lock 220 is too far from the tip of intravenous end 44 of needle 40 to slide axially beyond the tip in a manner that could permit re-exposure of the used needle. Hence, second cannula lock 220 provides greater resistance to an unauthorized attempt to re-expose the used needle and is much more likely to break or permanently damage a used needle in response to an excessive force exerted on shield 140 in an opening direction.

The extreme rear ends of sidewalls 174 on collar engaging area 166 include rounded ears 194 that project toward one another from opposed inner surfaces 175 of sidewalls 174. Rounded ears 194 are disposed to engage detents 118 on collar 90. More particularly, each rounded ear 194 includes a distal surface 195, a proximal surface 197 and a curved surface 198 extending between distal and proximal surfaces 195 and 197. Distal surface 194 is aligned to sidewall 174 at a rake angle of approximately 60° and proximal surface 197 is aligned to sidewall 174 at an angle of approximately 45°. Curved surface 198 extends smoothly and convexly between distal and proximal surfaces 195 and 197. Proximal surfaces 197 of rounded ears 194 will engage detents 118 to deflect sidewalls 174 slightly away from one another as shield 140 approaches the second position. The apex of curved surface 198 on each rounded ear 194 passes the respective rounded end surface 124 on chevron-shaped projection 118 on collar 90. As a result, sidewalls 174 begin to return resiliently toward an undeflected condition. The resilient return of sidewalls 174 and raked distal surface 195 of ears 194 causes sidewalls 174 to snap against chevron-shaped projection 118. This snapping action provides a clear audible and tactile indication of complete shielding and occurs substantially when the used needle is trapped by cannula finger lock 167 and cannula side latch 220. The angles of distal and proximal surfaces 195 and 197 of rounded ears 194 affect the performance of shield 140. In particular, a smaller acute angle alignment of proximal face 197 reduces the force required to move shield 140 passed rounded ears 194. A larger acute angle proximal surface 197 of rounded ears 194 requires a greater force to move shield 140 toward the second position. Similarly, the angle between distal surface 195 and sidewall 174 affects the acceleration characteristics as shield 140 is propelled toward the second position in response to the resilient return of sidewalls 174. This change in acceleration characteristics affects the audible indication of shielding. Different audible and acceleration characteristics can be achieved by employing more sharply pointed corners on the end surface of chevron-shaped projection 118 for engagement by rounded ears 194 of shield 140.

Top finger guide area 172 comprises a first ramp 184 that extends slightly on an upwardly slope from the rearward end of the collar engaging area to a shoulder 186. From shoulder 186 extends a second ramp 188 which slopes downwardly towards top section 163. Most preferably, first ramp 184 comprises touch bumps 190. The touch bumps provide a tactile and visual guide to alert the user that the user's finger has contacted the shield and that the shield is in a defined or controlled position. The touch bumps may be any configuration so long as they extend and are distinct from the top finger guide area. The touch bumps may also be of a distinguishing color as compared to the top finger guide area or the shield.

Second ramp 188 has interior surface 192 for urging the needle toward the center of slot 160 as the shield is being rotated into the closed position. The exterior surfaces are slightly inclined and extending radially from the second ramp. The interior surfaces are especially helpful if the longitudinal axis of the needle is misaligned with respect to the longitudinal axis of the hub.

Extending arms 180 are located at rearward end 168 and at the beginning of top finger area 172 and hold hanger bar 182.

The safety shield assembly and the needle assembly are assembled together whereby needle 40 is connected to hub 60 and sealed with adhesive at the ends of the hub. Hub 60 is then joined with collar 90 by ultra-sonic welding techniques or any other bonding techniques, or mechanical fit, whereby rearward annular skirt 94 of collar 90 mates with ribbed end 66 of the hub. Male ribs 82 of the hub are contained or forced fitted within inner sidewall 102 of rearward annular skirt 94 of collar 90. The collar is aligned with the intravenous end of the needle whereby the hook arm is aligned with the bevel up of the needle. Then rigid sleeve 50 is force fitted into inner side wall 96 of forward skirt 92 of collar 90 to cover the needle. Thereafter, shield 140 is connected to collar 90 whereby hanger bar 182 is force fitted into hook member 114 whereby slot 160 faces rigid sleeve 50. Most preferably, the shield is connected to the collar by a force fit or interference fit between the hanger bar and the hook bar. Therefore, the shield is always oriented in a stable position and will not move unless movement of the shield is positively initiated by the user. To assemble the last piece, shield 140 is moved towards rigid sleeve 50 and second rigid sleeve 52 is force fitted onto outer sidewall 104 of rearward skirt 94 of collar 90.

In addition, a label 196 may be applied to the finally assembled parts. The label may be used to prevent tamper resistance of the parts, so that they are not reused.

Figure 9:
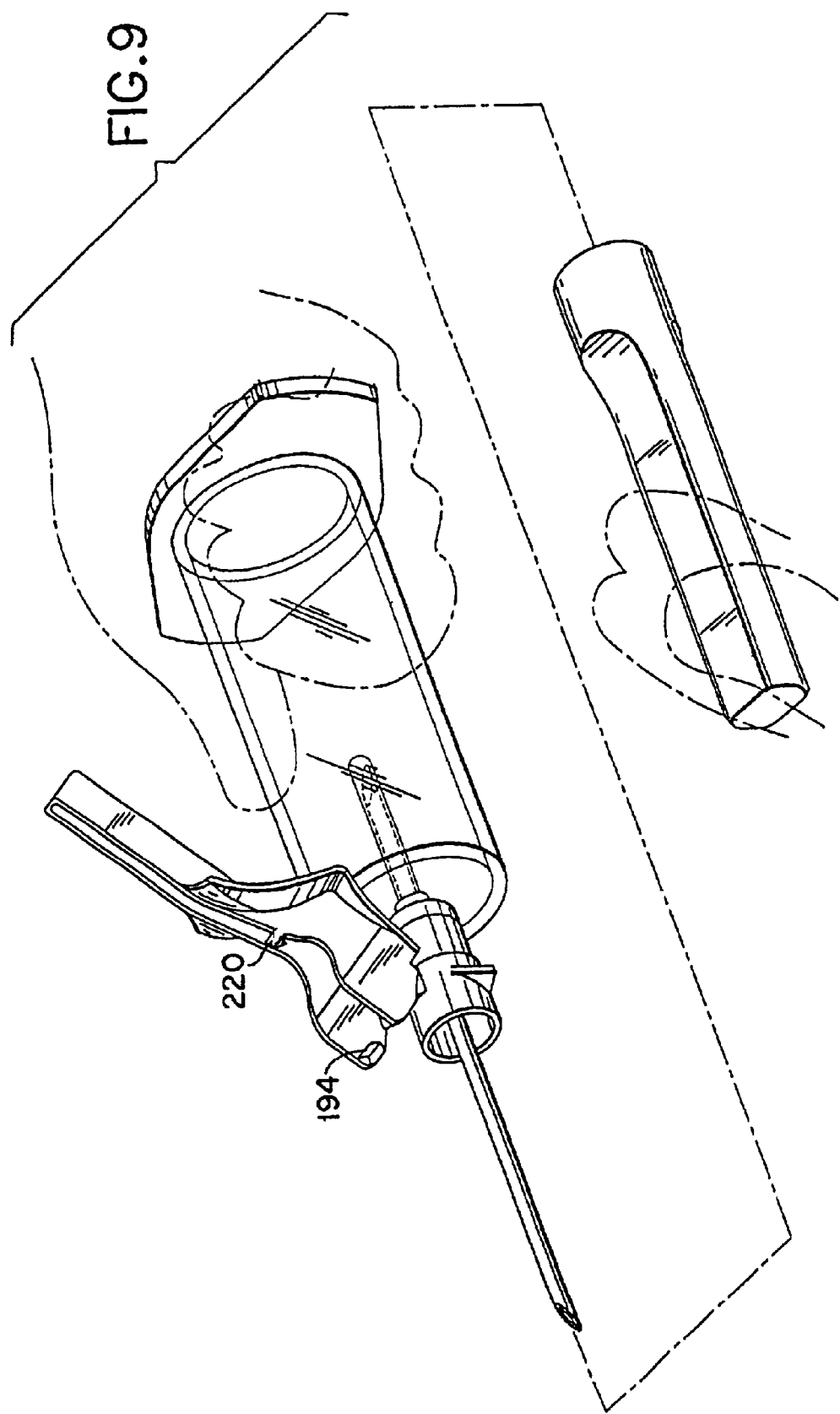
Figure 10:
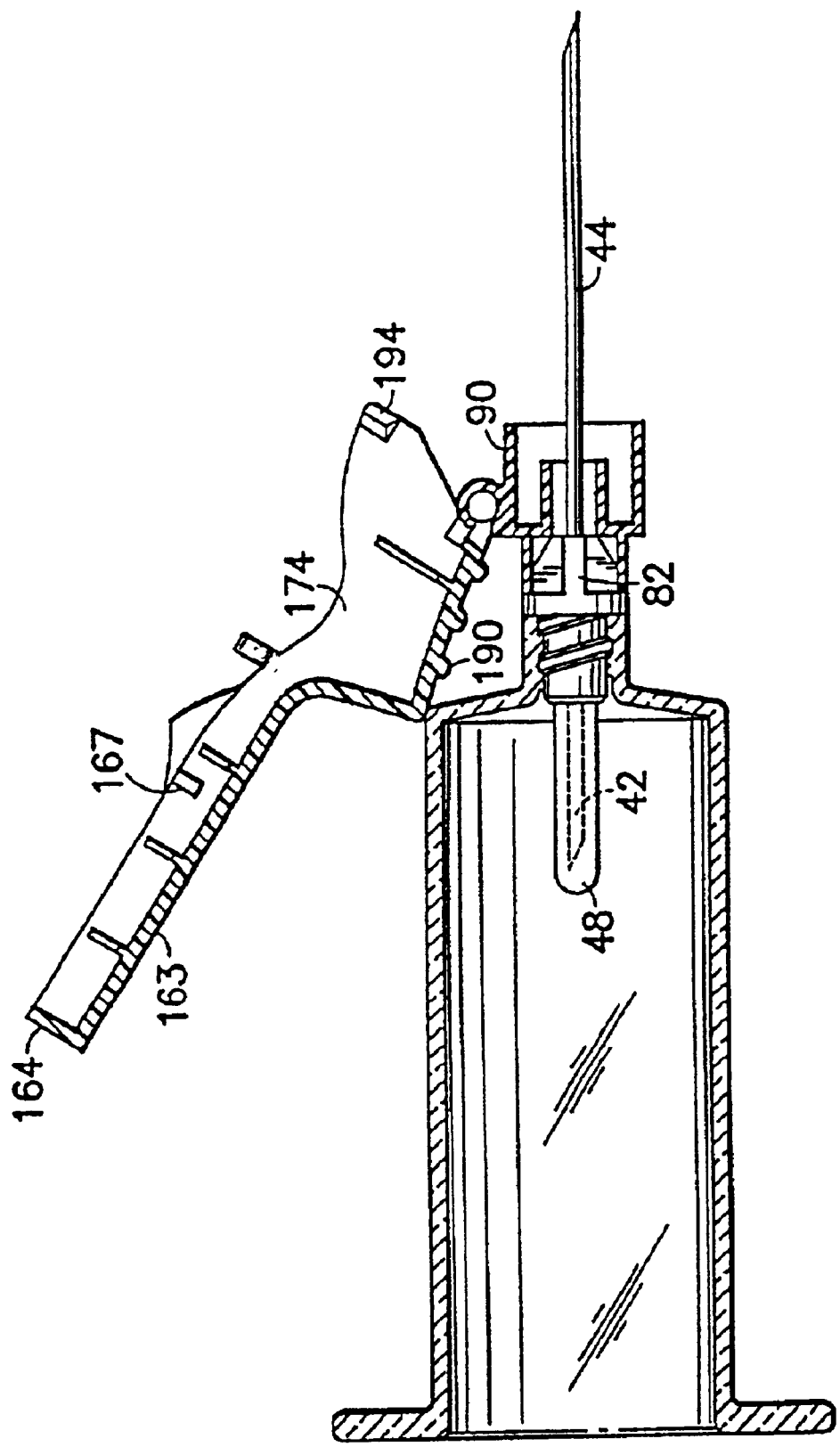
Figure 11:
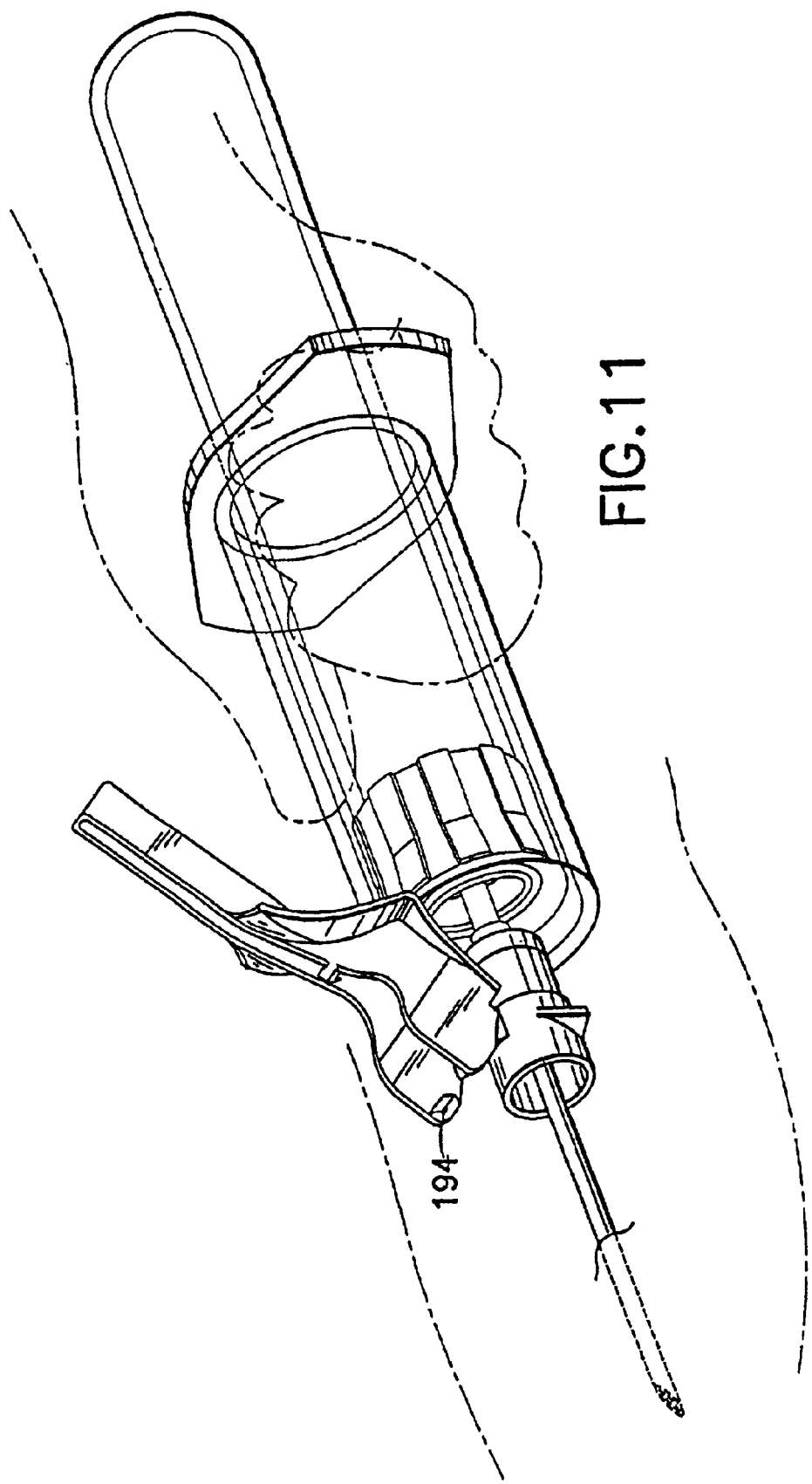
Figure 12:
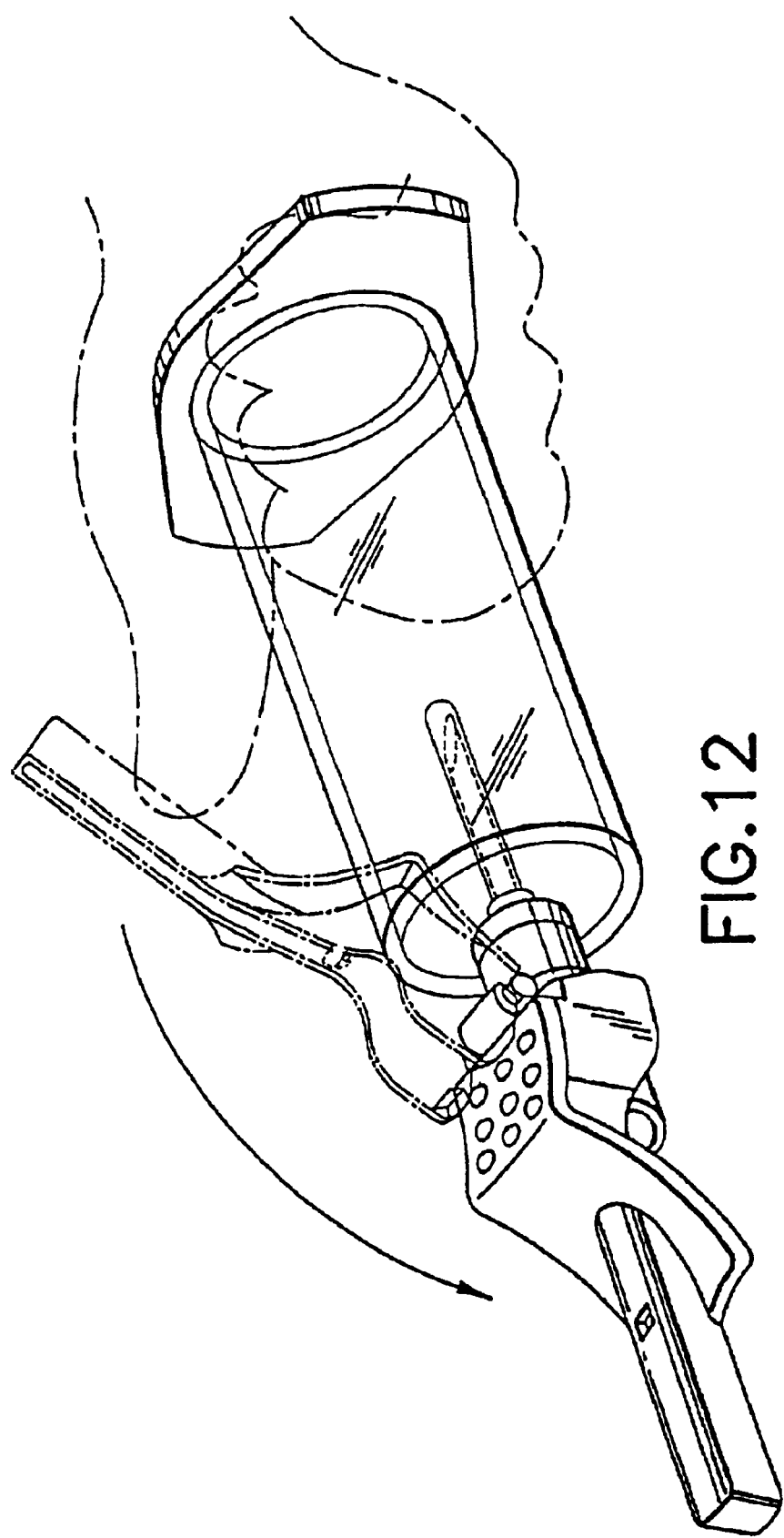
FIG. 12 is a cross sectional view of the assemblies in use with a conventional needle holder as shown in FIG. 9 taken along lines 12—12 thereof.

In use, as shown in FIGS. 7-15, the non-patient needle shield is removed and then a needle holder is screwed onto the hub of the needle. As specifically shown in FIGS. 8 and 12 the shield is then rotated back by the user towards the needle holder. Then as shown in FIG. 9, the intravenous needle shield is removed from covering the intravenous needle. Then as shown in FIG. 10, a venipuncture is conducted whereby the intravenous end of the needle is inserted into a vein of a patient and an evacuated tube having a closure is inserted into the needle holder. Then as shown in FIGS. 11 and 13, when the venipuncture is complete the user easily rotates the shield from the first position towards the intravenous needle to an intermediate position and then the user pushes on the shield at the top finger guide area to move the shield into a second position whereby the needle is trapped in the longitudinal opening.

Figure 16:
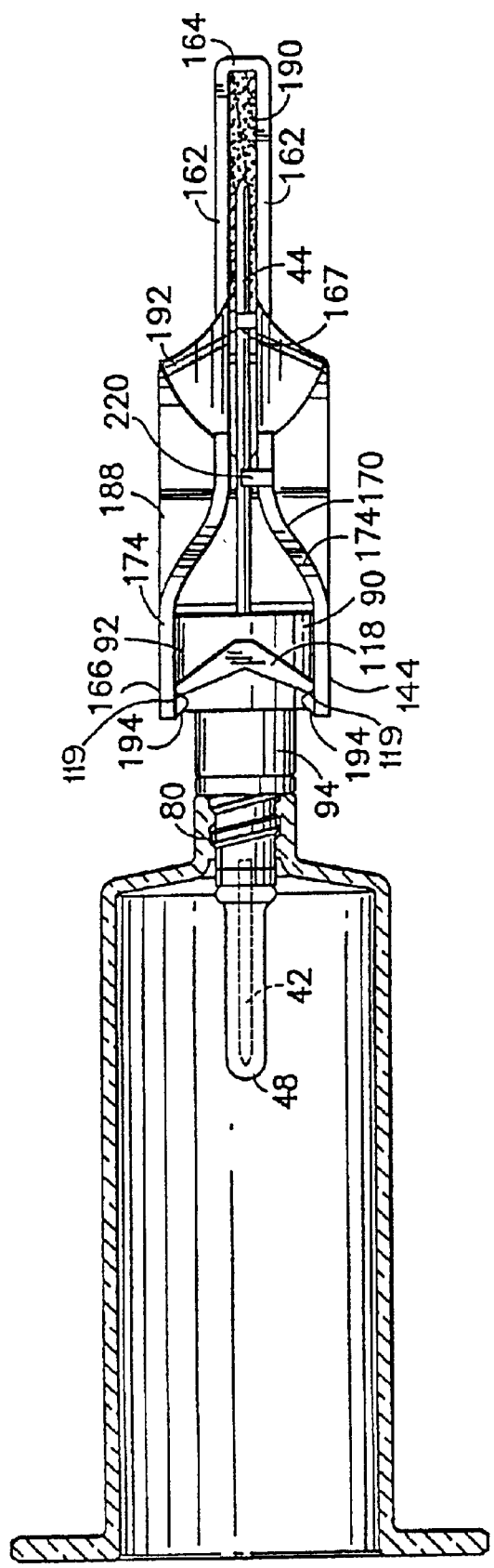
FIG. 16 illustrates an additional embodiment of the present invention, whereby a gel material is located in the shield as shown in a bottom view of the assemblies of FIG. 11.

The needle is contained within the shield as the shield is pivoted into the second position, whereby the needle snaps past first and second cannula locks 167 and 220 and is trapped as shown in FIGS. 14 and 15. Rounded projections 198 move over detents 118. This causes sidewalls 174 to deflect away from one another and then to snap back into engagement with collar 90 to provide a clear audible and tactile indication of complete shielding. The rounded configuration of projections 198 ensures easy movement of shield 140, without sacrificing the locking retention attributable to cannula locks 167 and 200. Alternatively as shown in FIG. 16, a gel material 190 is located at first cannula lock 167 so that when the needle snaps past cannula locks 167 and 220 it will come to rest in gel material 190. The gel material will contain any residual fluid that may be on the needle.

Figure 17:
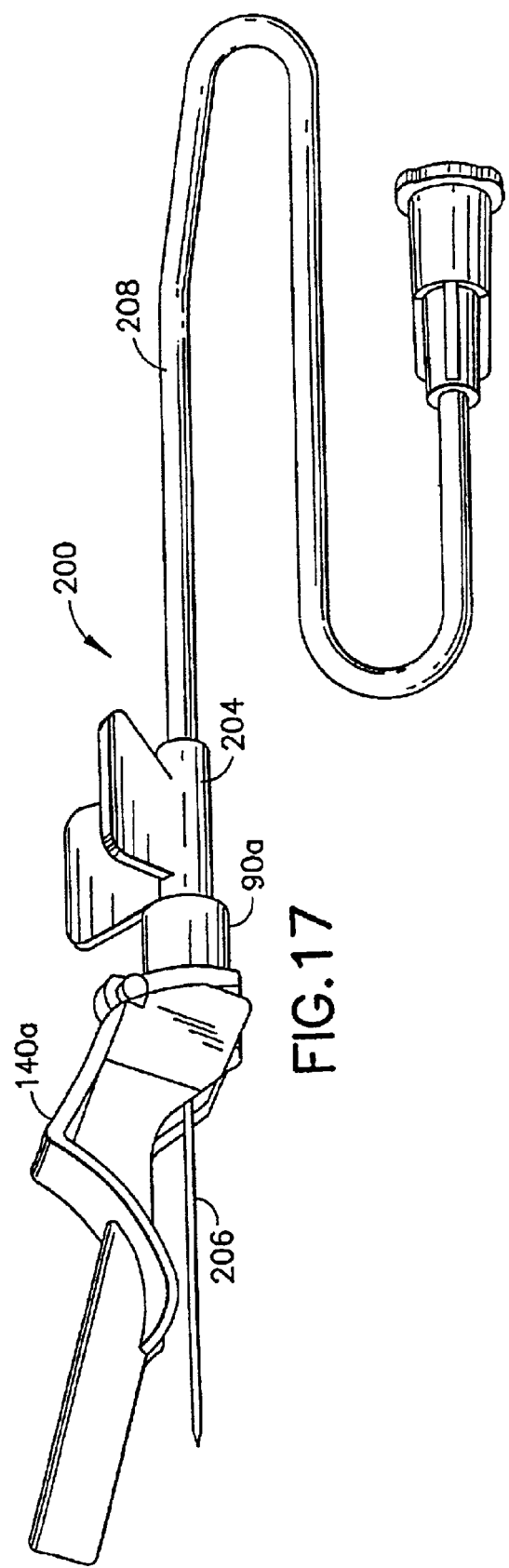
FIG. 17 is a perspective view of an additional embodiment of the present invention in use with a blood collection set.
Figure 18:
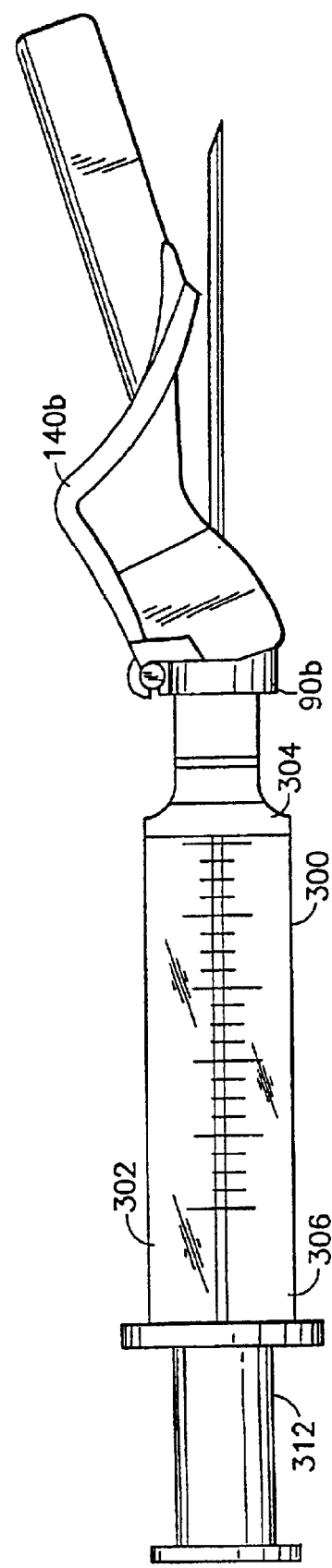
FIG. 18 is a perspective view of an additional embodiment of the present invention in use with a syringe.
Figure 19:
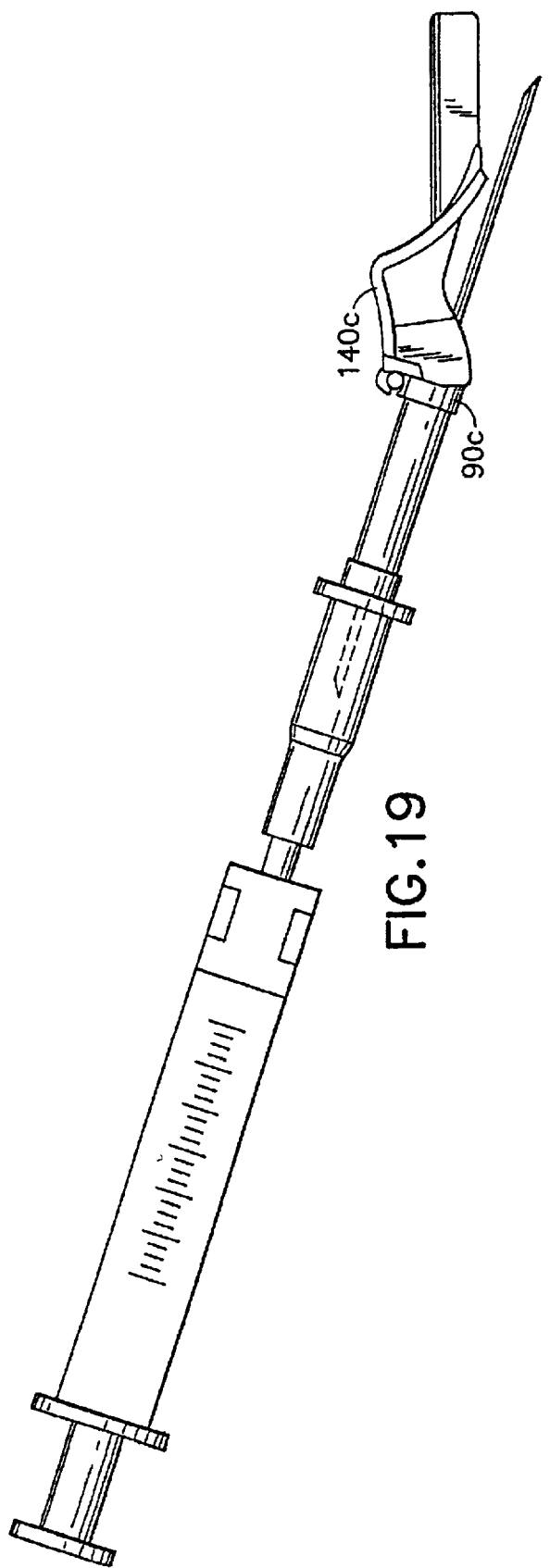
FIG. 19 is a perspective view of an additional embodiment of the present invention in use with a catheter.

FIGS. 17, 18, and 19 are further embodiments of the invention that may include components which are substantially identical to the components of FIGS. 1–3. Accordingly, similar components performing similar functions will be numbered identically to those components of FIGS. 1–3, except that a suffix "a" will be used to identify those similar components in FIG. 17, a suffix "b" will be used to identify those similar components in FIG. 18 and a suffix "c" will be used to identify those similar components in FIG. 19.

Alternatively, the safety shield assembly of the present invention may be used in conjunction with a conventional intravenous (IV) infusion set, as illustrated in FIG. 17.

For purposes of illustration, shield 140a and collar 90a are connected to a conventional IV infusion set, 200, or butterfly structure comprising a needle body with a needle hub 204 extending from the forward end of the needle body and a needle 206 embedded in hub 204. Extending from the rearward end of the needle body is flexible tubing 208 which is conventional and utilized to allow the user to manipulate the structure and to connect it subsequently to supplies of infusion liquids or for the return of collected blood if the arrangement is being used to collect blood.

Infusion set 200 further comprises flexible wings 210 attached to and projecting outwardly from needle hub 204.

Alternatively, the safety shield assembly of the present invention may be used in conjunction with a syringe, as illustrated in FIG. 18.

For purposes of illustration, shield 140b and collar 90b are connected to a conventional hypodermic syringe 300 comprising a syringe barrel 302 having a distal end 304 a proximal end 306 and a plunger 312.

Alternatively, the present invention may be used in conjunction with a catheter as illustrated in FIG. 19.

Figure 20:
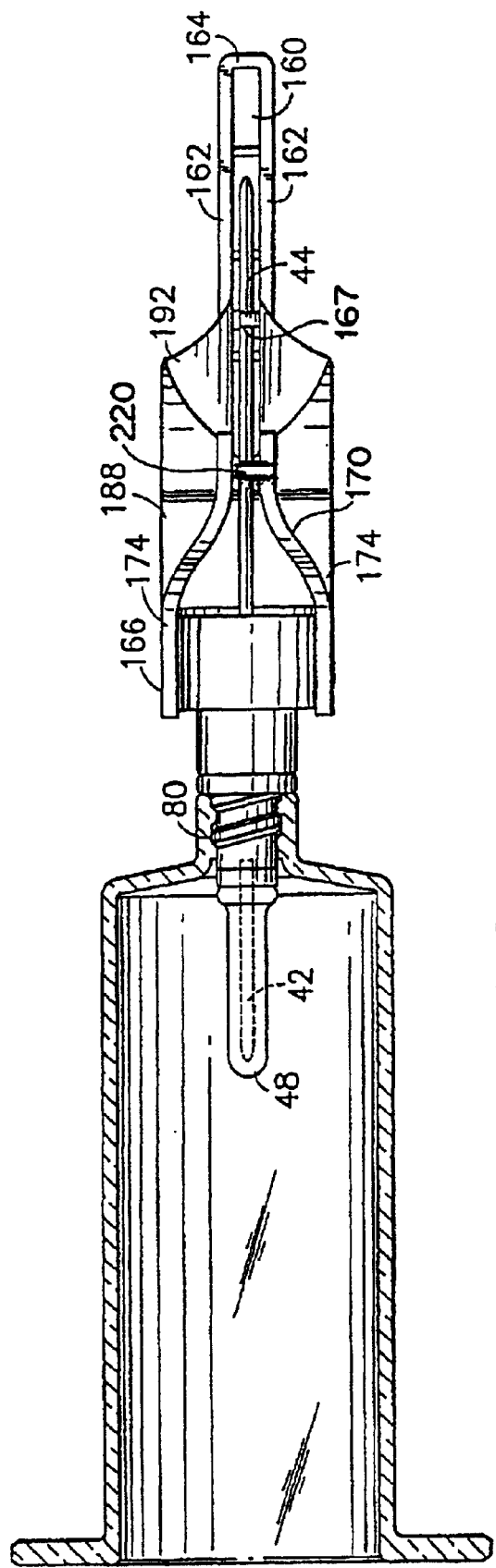
FIG. 20 is a bottom view of the assembly, similar to FIG. 15A, but showing an additional embodiment of the present invention without a chevron-shaped structure on the collar and without locking ears on the shield.

A further alternate embodiment is illustrated in FIG. 20, and is virtually identical to the embodiment of the invention depicted in FIG. 15A. As a result, comparable numerals have been employed to identify identical or very similar components. FIG. 20, however, differs from FIG. 15A in that collar 90 does not have the chevron-shaped protrusion 118 illustrated in FIG. 15A. Additionally, shield 140 does not have ears comparable to rounded ears 194 of FIG. 15A. Thus, the embodiment illustrated in FIG. 20 relies entirely upon the engagement of first and second cannula finger locks 167 and 220 with needle 40. There are fewer structures on the embodiment of FIG. 20 to achieve the clear audible and tactile indication of complete shielding as in the previous embodiment and no structure for accelerating shield 140 in to the second position around needle 40. However, upon complete shielding, the retention between shield 140 and needle 40 in the embodiment of FIG. 20 is comparable to the retention achieved by the previous embodiments.

The shield and collar of the safety shield assembly of the present invention are comprised of moldable parts which can be mass produced from a variety of materials including, for example, polyethylene, polyvinyl chloride, polystryene or polyethylene and the like. Materials will be selected which will provide the proper covering and support for the structure of the invention in its use, but which will provide also a degree of resiliency for the purpose of providing the cooperative movement relative to the shield and the collar of the assembly.

What is claimed is:

1. A safety needle assembly comprising a needle cannula, a needle hub mounted to said needle cannula, a protrusion formed on said hub, said protrusion being formed with forward and rearward surfaces, and end surfaces extending between the forward and rearward surfaces, a shield having proximal and distal ends, said proximal end of said shield being hingedly mounted to said hub for rotation from a first position where said shield is spaced from said needle cannula to a second position where said shield substantially surrounds said needle cannula, said shield comprising a top wall and opposed sidewalls extending from said top wall, said side walls having bottom edges, a rounded projection formed on at least one of said side walls, a resiliently deflectable distal cannula lock projecting from one of said distal sidewalls angularly toward said top wall, and a proximal cannula lock having a base leg projecting from said bottom edge of one of said sidewalls in a direction away from said top wall and a resiliently deflectable cannula engaging leg projecting from an end of said base leg furthest from said top wall angularly back toward said top wall, whereby said distal cannula lock and said cannula engaging leg of said proximal cannula lock being configured for lockingly engaging said needle cannula when said shield reaches said second positron and whereby said rounded projection on said shield is disposed for engaging said protrusion on said hub when said shield approaches said second position.

2. The safety needle assembly of claim 1, wherein said protrusion comprises two end surfaces and wherein each of said sidewalls has a rounded projection disposed for engaging the respective end surfaces of the protrusion.

3. The safety needle assembly of claim 2, wherein each said rounded projection includes a slanted proximal face for engaging said end surfaces of said protrusion and resiliently defecting said side walls away from one another as said shield approaches said second position and a slanted distal face for cooperating with said protrusion and said resiliently deflected sidewalls for accelerating said shield into said second position.

4. The safety needle assembly of claim 3, wherein said shield is unitarily formed from a plastic material.

5. The safety shield assembly of claim 3, wherein said needle hub comprises art inner tubular portion securely mounted to said needle cannula and an outer collar securely mounted over said inner tubular portion, said shield being hingedly mounted to said collar of said hub.

6. The safety needle assembly of claim 3, wherein said needle cannula includes a proximal end, said needle cannula extending entirely through said passage of said hub such that said proximal end of said needle cannula projects proximally beyond said proximal end of said hub.

7. The safety needle assembly of claim 6, further comprising an elastomeric sleeve mounted over said proximal end of said needle cannula and securely engaged to said proximal end of said hub.

8. The safety needle assembly of claim 1, wherein said end surface of said protrusion is a rounded surface extending continuously between said forward and rearward surfaces of said protrusion.

9. A safety needle assembly comprising a needle cannula, a needle hub mounted to said needle cannula, a protrusion formed on said needle hub, said protrusion having forward and rearward surfaces aligned at an acute angle to said needle cannula and rounded ends extending between said forward and rearward surfaces, a shield having proximal and distal ends, said proximal end of said shield being hingedly mounted to said hub for rotation from a first position where said shield is spaced from said needle cannula to a second position where said shield substantially surrounds said needle cannula, said shield comprising a distal portion and a proximal portion, said distal portion of said shield including a distal top wall and opposed distal sidewalls extending from said distal top wall, said proximal portion of said shield comprising a proximal top wall and opposed proximal sidewalls extending from said proximal top wall, said proximal sidewalls having bottom edges, said proximal sidewalls being spaced from one another at said proximal end of said shield for receiving said needle hub therebetween, said proximal sidewalls converging toward one another and joining said distal sidewalls, said needle shield further comprising:

- a resiliently deflectable distal cannula look extending from one of said distal sidewalls and projecting angularly toward said distal top wall;
- a proximal cannula lock having a base leg projecting from the bottom edge of one said proximal sidewall in a direction away from said proximal lop wall and a resiliently deflectable cannula engaging leg extending from an end of said base leg furthest from said proximal top wall and projecting angularly back toward said proximal top wall; and
- at least one rounded projection on said proximal portion and configured for snapped engagement with one of said end surfaces of said protrusion on said hub;
- whereby said distal cannula lock and said cannula engaging leg of said proximal cannula lock are configured to trap said needle cannula when said shield reaches said second position, and whereby said rounded projection engages said end surface of said protrusion to propel said shield to said second position.

10. The safety needle assembly of claim 9, wherein said protrusion comprises two end surfaces and wherein said at least one rounded projection comprises two rounded projections.

11. The safety needle assembly of claim 10, wherein said rounded projections are formed on said proximal sidewalls.

12. The safety needle assembly of claim 11, wherein said proximal cannula lock is at a location on said proximal sidewall converging toward said distal sidewall.

13. The safety needle assembly of claim 11, wherein said shield is formed unitarily from a plastic material.

14. The safety shield assembly of claim 11, wherein said needle hub comprises an inner tubular portion securely mounted to said needle cannula and an outer collar securely mounted over said inner tubular portion, said shield being hingedly mounted to said collar of said hub.

15. The safety needle assembly of claim 11, wherein said needle cannula includes a proximal end, said needle cannula extending entirely through said passage of said hub such that said proximal end of said needle cannula projects proximally beyond said proximal end of said hub.

16. The safety needle assembly of claim 15, further comprising an elastomeric sleeve mounted over said proximal end of said needle cannula and securely engaged to said proximal end of said hub.

17. The safety needle assembly of claim 9, wherein said needle cannula includes a proximal end, said needle cannula extending entirely through said passage of said hub such that said proximal end of said needle cannula projects proximally beyond said proximal end of said hub.

18. The safety needle assembly of claim 9, further comprising an elastomeric sleeve mounted over said proximal end of said needle cannula and securely engaged to said proximal end of said hub.

19. The safety needle assembly of claim 9, further comprising a medical device connected to said needle hub.

20. The safety needle assembly of claim 19, wherein the medical device comprises a holder for releasably receiving a fluid collection tube.

21. The safety needle assembly of claim 19, wherein the medical device is a syringe.

22. The safety needle assembly of claim 19, wherein the medical device comprises an intravenous infusion set.

23. The safety needle assembly of claim 9, wherein said end surface of said protrusion is a rounded surface extending continuously between said forward and rearward surfaces of said protrusion.

24. A safety needle assembly comprising a needle cannula, a needle hub mounted to said needle cannula, a shield having proximal and distal ends, said proximal end of said shield being hingedly mounted to said hub for rotation from a first position where said shield is spaced from said needle cannula to a second position where said shield substantially surrounds said needle cannula, said shield comprising a top wall and opposed sidewalls extending from said top wall, said side walls having bottom edges, a resiliently deflectable distal cannula lock projecting from one of said distal sidewalls angularly toward said top wall, and a proximal cannula lock having a base leg projecting from said bottom edge of one of said sidewalls in a direction away from said top wall and a resiliently deflectable cannula engaging leg projecting from an end of said base leg furthest from said top wall angularly back toward said top wall, whereby said distal cannula lock and said cannula engaging leg of said proximal cannula lock being configured for lockingly engaging said needle cannula when said shield reaches said second position.

25. The safety needle assembly of claim 24, wherein said shield is unitarily formed from a plastic material.

* * * * *